US010967373B2

United States Patent
Astier et al.

(10) Patent No.: US 10,967,373 B2
(45) Date of Patent: Apr. 6, 2021

(54) ELECTRO-FLUIDIC FLOW PROBE

(71) Applicant: International Business Machines Corporation, Armonk, NY (US)

(72) Inventors: Yann Andre Nicolas Astier, Irvington, NY (US); Jingwei Bai, Los Angeles, CA (US); Young Hoon Kwark, Chappaqua, NY (US); Stanislav Polonsky, Putnam Valley, NY (US); Joshua T. Smith, Croton on Hudson, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 378 days.

(21) Appl. No.: 14/744,099

(22) Filed: Jun. 19, 2015

(65) Prior Publication Data

US 2015/0300973 A1    Oct. 22, 2015

Related U.S. Application Data

(63) Continuation of application No. 14/573,135, filed on Dec. 17, 2014.
(Continued)

(51) Int. Cl.
*B01L 3/00* (2006.01)
*H01L 21/66* (2006.01)
(Continued)

(52) U.S. Cl.
CPC ...... *B01L 3/50273* (2013.01); *G01N 27/4473* (2013.01); *G01N 27/44791* (2013.01);
(Continued)

(58) Field of Classification Search
CPC ......... B01L 3/50273; B01L 2400/0421; B01L 2300/0627; B01L 2300/0645;
(Continued)

(56) References Cited

U.S. PATENT DOCUMENTS

| 6,358,395 B1 * | 3/2002 | Schorzman ............ B01D 61/08 204/228.3 |
| 2006/0180469 A1 * | 8/2006 | Han .................. G01N 27/44791 204/601 |

(Continued)

FOREIGN PATENT DOCUMENTS

JP    10246721    * 9/1998

OTHER PUBLICATIONS

List of IBM Patents or Patent Applications Treated as Related; Date Filed: Jun. 19, 2015, pp. 1-2.
(Continued)

*Primary Examiner* — Michael Y Sun
(74) *Attorney, Agent, or Firm* — Cantor Colburn LLP; Rabin Bhattacharya

(57) ABSTRACT

An apparatus for an electro-fluidic flow probe includes a body portion including an electro-fluidic bias tee for receiving (i) a fluid electrolyte and (ii) an electrical connection for providing an electrical potential to the fluid electrolyte; a first inlet including a tube extending from the first inlet to an outlet through the electro-fluidic bias tee; and a second inlet including the electrical connection having a wire that extends from the second inlet to the outlet through the electro-fluidic bias tee to transfer the electrical potential to a device under test.

13 Claims, 7 Drawing Sheets

Related U.S. Application Data

(60) Provisional application No. 61/980,113, filed on Apr. 16, 2014.

(51) Int. Cl.

| | |
|---|---|
| *G01N 27/447* | (2006.01) |
| *G01N 27/453* | (2006.01) |
| *G01R 31/26* | (2020.01) |
| *B81B 1/00* | (2006.01) |
| *A61B 5/1486* | (2006.01) |
| *A61B 5/0476* | (2006.01) |
| *G01N 27/08* | (2006.01) |
| *G01N 27/07* | (2006.01) |
| *G01N 33/487* | (2006.01) |
| *G01N 27/403* | (2006.01) |

(52) U.S. Cl.
CPC ....... *G01N 27/453* (2013.01); *G01R 31/2601* (2013.01); *H01L 22/14* (2013.01); *A61B 5/0476* (2013.01); *A61B 5/14865* (2013.01); *A61B 2562/0209* (2013.01); *B01L 3/502715* (2013.01); *B01L 2300/0627* (2013.01); *B01L 2300/0645* (2013.01); *B01L 2400/0421* (2013.01); *B81B 1/004* (2013.01); *G01N 27/07* (2013.01); *G01N 27/08* (2013.01); *G01N 27/403* (2013.01); *G01N 33/48721* (2013.01); *H01L 22/00* (2013.01); *H01L 22/12* (2013.01)

(58) Field of Classification Search
CPC .... B01L 3/502715; H01L 22/14; H01L 22/00; H01L 22/12; G01R 31/2601; G01N 27/44791; G01N 27/4473; G01N 27/453; G01N 27/08; G01N 27/07; G01N 33/48721; G01N 27/403; A61B 5/14865; A61B 2562/0209; A61B 5/0476; B81B 1/004

See application file for complete search history.

(56) References Cited

U.S. PATENT DOCUMENTS

| | | | |
|---|---|---|---|
| 2007/0215528 A1* | 9/2007 | Hayenga | B01L 3/502761 209/576 |
| 2010/0327255 A1* | 12/2010 | Peng | B82Y 10/00 257/9 |
| 2010/0327874 A1* | 12/2010 | Liu | G01N 33/48721 324/464 |
| 2012/0037508 A1* | 2/2012 | Shiraki | G01N 27/44713 204/453 |
| 2012/0103821 A1* | 5/2012 | Harrer | B81C 1/00071 205/84 |
| 2013/0075257 A1* | 3/2013 | Howell, Jr. | G01N 27/44795 204/450 |
| 2014/0131204 A1* | 5/2014 | Chou | B03C 5/005 204/452 |

OTHER PUBLICATIONS

Yann Andre Nicolas Astier, et al.,"Electro-Fluidic Flow Probe," U.S. Appl. No. 14/573,135, filed Dec. 17, 2014.

* cited by examiner

600

605

| 11 | 21 | 31 | 41 | 51 | 61 | 71 | 81 | 91 | A1 | B1 |
|---|---|---|---|---|---|---|---|---|---|---|
|    | 10 | 4  | 10 | 0  | 0  | 5  | 4  | 6  | inf |   |
| 12 | 22 | 32 | 42 | 52 | 62 | 72 | 82 | 92 | A2 | B2 |
|    | 16 | 8  | 1  | 3  | 5  | 6  | 9  | inf | 7 |   |
| 13 | 23 | 33 | 43 | 53 | 63 | 73 | 83 | 93 | A3 | B3 |
|    | 7  | 0  | 0  | 3  | 6  | 4  | 6  | 2  | 5  |   |
| 14 | 24 | 34 | 44 | 54 | 64 | 74 | 84 | 94 | A4 | B4 |
|    | 0  | 3  | 2  | 8  | 5  | 6  | 0  | 5  | 0  |   |
| 15 | 25 | 35 | 45 | 55 | 65 | 75 | 85 | 95 | A5 | B5 |
|    | inf | 0 |    |    |    | 8  | 1  | 5  | 0  |   |
| 16 | 26 | 36 | 46 | 56 | 66 | 76 | 86 | 96 | A6 | B6 |
|    | dam | 2 | 0 | 4 |    | 4  | 2  | 3  | 4  |   |
| 17 | 27 | 37 | 47 | 57 | 67 | 77 | 87 | 97 | A7 | B7 |
|    | inf | 5 | 0 | 3 | 2 | 70 | 55 | 20 | inf |   |
| 18 | 28 | 38 | 48 | 58 | 68 | 78 | 88 | 98 | A8 | B8 |
|    | inf | 0 | 6 | 6 | 6 | 70 | 0 | inf | inf |   |
| 19 | 29 | 39 | 49 | 59 | 69 | 79 | 89 | 99 | A9 | B9 |
|    | 1  | inf | 30 | inf | inf | inf | 0 | inf | inf |   |
| 1A | 2A | 3A | 4A | 5A | 6A | 7A | 8A | 9A | AA | BA |
|    |    | 8  | 1  | inf | 0 | 3 | inf | inf | inf |   |
| 1B | 2B | 3B | 4B | 5B | 6B | 7B | 8B | 9B | AB | BB |
|    | 7  | 9  | 6  | 0  | 0  | 0  | inf | 0 | inf |   |

FIG. 6

ELECTRO-FLUIDIC FLOW PROBE

DOMESTIC PRIORITY

This application is a continuation of U.S. patent application Ser. No. 14/573,135, filed Dec. 17, 2014, which claims priority to U.S. Provisional Application No. 61/980,113, entitled "ELECTRO-FLUIDIC FLOW PROBE," filed Apr. 16, 2014, which is incorporated herein by reference in its entirety.

BACKGROUND

The present invention is related to wet wafer-level testing, more particularly the testing of a chip on a wafer using an electro-fluidic flow probe.

An increasing number of silicon and carbon based wafer manufacturing is now directed to taking place in liquid. It is desired to have a cost-effective and efficient method for such testing.

Wet wafer-level testing is generally carried out on chip level, which means a test is performed on each chip after dicing, bonding, encapsulation, and mounting. Wafers are thin, circular slices of doped silicon from which integrated circuits or its semiconductor devices are built. The testing can be done to select and determine the non-usable chips in the wafer. The dicing, bonding, encapsulation, and packaging costs can be the essential part of the total production costs and can be considered wasted for the non-functional or usable chips. This method is time consuming and can take approximately ten minutes per chip resulting in high manufacturing costs. There is a need for wet wafer-level testing to identify defects in the earlier stages of production so that substantial costs are not used on non-usable chips. The present invention describes an apparatus, method, and system to perform wafer-level testing of chips in liquid media in a more cost-effective and efficient manner.

SUMMARY

One aspect of the present invention is an electro-fluidic flow probe which includes: a body portion including an electro-fluidic bias tee for receiving (i) a fluid electrolyte and (ii) an electrical connection for providing an electrical potential to the fluid electrolyte; a first inlet including a tube extending from the first inlet to an outlet through the electro-fluidic bias tee; and a second inlet including the electrical connection having a wire that extends from the second inlet to the outlet through the electro-fluidic bias tee to transfer the electrical potential to a device under test.

Another aspect of the present invention is a method for testing a nanochannel in a wafer. The method includes: connecting a first electro-fluidic flow probe to a first north fluidic port of the nanochannel; connecting a second electro-fluidic flow probe to a first south fluidic port of the nanochannel; filling a north microchannel with an electrical potential, wherein the electrical potential is delivered from the first electro-fluidic flow probe to the first north fluidic port and into the north microchannel; filling a south microchannel with an electrical potential, wherein the electrical potential is delivered from the second electro-fluidic flow probe to the first south fluidic port and into the south microchannel; and measuring a current between the first electro-fluidic flow probe and the second electro-fluidic flow probe to verify an electrical contact between the north microchannel and the south microchannel.

Another aspect of the present invention provides a system for testing a nanochannel. The system includes: a wafer with at least one nanochannel; a first electro-fluidic flow probe connected to a first north fluidic port of the nanochannel, where the first electro-fluidic flow probe fills a north microchannel with an electrical potential; a second electro-fluidic flow probe connected to a first south fluidic port of the nanochannel, where the second electro-fluidic flow probe fills a south microchannel with an electrical potential; and a measuring instrument for measuring the current between the north microchannel and the south microchannel.

Another aspect of the present invention provides a method to test a nanopore. The method includes filling a testing bath with a liquid buffer; placing a wafer on top of the liquid buffer, the wafer includes at least one nanopore; applying an electrical potential to the nanopore using an electro-fluidic flow probe, where the electrical potential makes an electrical contact with the liquid buffer; and measuring a current of the nanopore.

Another aspect of the present invention provides a system for testing a nanopore. The system includes: a wafer with at least one nanopore; a testing bath filled with a liquid buffer, where the wafer is placed on top of the liquid buffer; an electro-fluidic flow probe for applying an electrical potential on the nanopore, where the electrical potential makes an electrical contact with the liquid buffer; and a device for measuring a current of the nanopore.

BRIEF DESCRIPTION OF THE DRAWINGS

The accompanying figures where like reference numerals refer to identical or functionally similar elements throughout the separate views, and which together with the detailed description are incorporated in and from part of the specification, serve to further illustrate various embodiments to explain various principles and advantages all in accordance with the present invention.

FIG. 6 shows an ionic current map generated for a wafer with nanopores according to a further embodiment of the present invention.

DETAILED DESCRIPTION

The above and other features of the present invention will become more distinct by a detailed description of embodiments shown in combination with attached drawings. Identical reference numbers represent the same or similar parts in the attached drawings of the present invention.

The terminology used herein is for the purpose of describing particular embodiments only and is not intended to be limiting of the present invention. As used herein, the singular forms "a", "an" and "the" are intended to include the plural forms as well, unless the context clearly indicated otherwise. It will be further understood that the terms "includes" and/or "including," when used in this specification, specify the presence of stated features, integers, steps, operations, elements, and/or components, but do not preclude the presence of addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiment was chosen and described in order to best explain the principles of the present invention and the practical application, and to enable others of ordinary skill in the art to understand the present invention for various embodiments with various modifications as are suited to the particular use contemplated.

As required, detail embodiments of the present invention are disclosed herein; however, it is to be understood that the disclosed embodiments are merely exemplary of the present invention, which can be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure. The terms and phrases used herein are not intended to be limiting but rather, to provide an understandable description of the present invention.

The present invention describes an electro-fluidic flow probe that can be used in wet wafer-level testing. The electro-fluidic flow probe merges the fluid with an electrical connection inside the probe and applies an electrical potential to a device under test which is embedded in a wafer.

Figure 1:
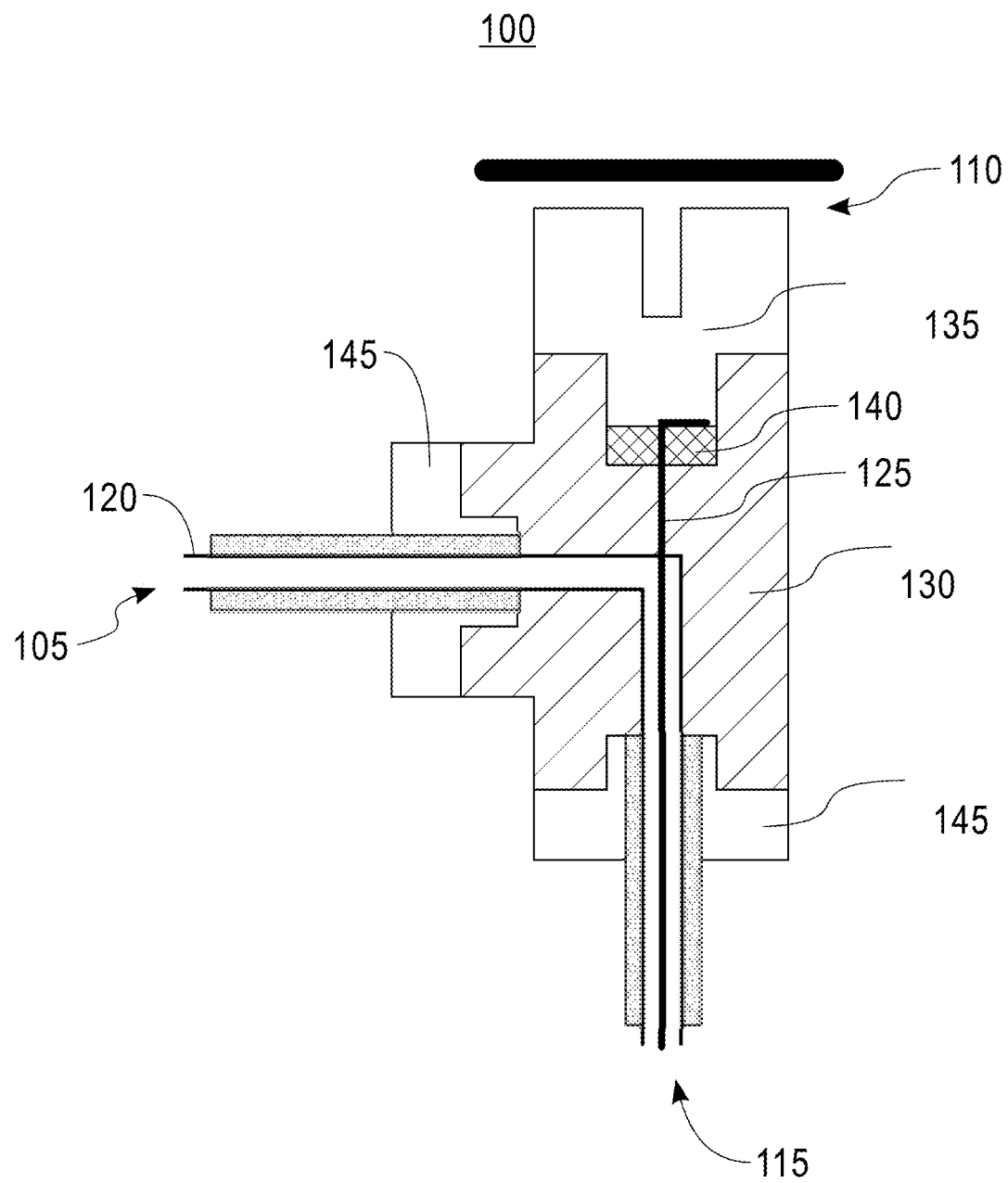
FIG. 1 shows an electro-fluidic flow probe according to an embodiment of the present invention.

FIG. 1 shows an electro-fluidic flow probe 100, according to an embodiment of the present invention. The electro-fluidic flow probe can be used in wet wafer-level testing, but it is not limited to such applications. The electro-fluidic flow probe has two inlets, a first inlet 105 and a second inlet 110. The first inlet 105 includes a tube 120 that extends to the outlet. The diameter of the tube can range from 1/16 inch to 1/32 inch. The first inlet is used for the input of a fluid electrolyte, which is typically a liquid with ionic conductivity. It is preferred to use distilled water for the fluid electrolyte, but applications are not limited as such and can vary as known by the person with the ordinary skill in the art.

Referring to FIG. 1, the second inlet 110 is an input for the electrical connection. A wire 125 is inserted that extends all the way to the outlet of the electro-fluidic flow probe. The electrical connection of the probe can be, but is not limited to, a copper coaxial cable that is inserted in a second inlet. The wire can be a copper coaxial cable that comes into contact with a plate of silver (Ag) or silver chloride (AgCl). In another embodiment of the present invention, the wire can be an Ag or AgCl wire. It is preferred to have an Ag or AgCl electrical connection that merges with the liquid because of its electrochemical properties of a sustained potential, however, the present invention is not limited to such applications. Referring to FIG. 1, the wire is inserted into the electro-fluidic bias tee 130 which is located inside the electro-fluidic flow probe. The electro-fluidic bias tee receives the fluid electrolyte from the first inlet and the electrical connection from the second inlet. The electro-fluidic bias tee includes a micro-machined device that communicates with the electrical connection and the fluid as to merge the fluid with the electrical connection to create a fluidic electrical potential. Similar electro-fluidic bias tees are used in electrophysiology's microelectrode cell recording as known to the ordinary person in the relevant art. In the electro-fluidic bias tee the wire 125 is inserted inside the tube 120 and is extended all the way to the outlet. The wire runs alongside with the fluid extending all the way to the end of the outlet 115 and provides an electrical potential to the device under test.

In another embodiment of the present invention a pressure source is connected to the first inlet. The pressure source is used for applying pressure to the fluid so that the fluid electrolyte passes through the electro-fluidic bias tee in a controlled fashion.

In another embodiment of the present invention the second inlet includes a socket 135 in which the wire is inserted into. It is preferred that the socket is from 1 mm to 5 mm in width and more preferably 2 mm in width.

In another embodiment of the present invention, a gasket 140 is located below the socket 135. It is preferred that the gasket 140 is made from silicon. Referring to FIG. 1, the silicon gasket is located between the socket 135 and an electro-fluidic bias tee 130. The gasket creates a leak tight connection between the second inlet and the electro-fluidic bias tee. Referring to FIG. 1, the wire 125 extends from the silicon gasket 140 to the outlet of the electro-fluidic flow probe.

In another embodiment of the present invention, a fitting 145 is used to seal the tube at the first inlet 105 to the electro-fluidic bias tee. Similarly, it is preferred for the outlet 115 to be secured to the electro-fluidic bias tee 130 with a fitting 145. According to an embodiment of the present invention, the fitting can be a rubber seal to fit around the first inlet 105 and a rubber seal to fit around the outlet 115 so that it is securely positioned on the electro-fluidic flow probe.

Referring to FIG. 1, the outlet 115 provides an electrical potential by applying a droplet of the electrical potential onto the device under test, which can be, but is not limited to, a device embedded in the wafer. The wire in the electro-fluidic flow probe runs alongside with the fluid resulting in minimal dead volume remaining in the electro-fluidic flow probe. Dead volume is created when very small quantities of a sample of liquid is utilized, and a large amount of sample fluid remains in a standard sample size tube and cannot be removed by the probe. The remaining fluid is wasted and the remaining tests can no longer be performed. Referring to FIG. 1, the wire 125 extends all the way to the output of the outlet 115 which as a result decreases the dead volume that remains in the electro-fluidic flow probe.

According to the present invention the parameters for the parts of the electro-fluidic flow probe can vary depending on the type of wafer being tested. Commercial off the shelf parts can be used in creating the electro-fluidic flow probe or custom parts can be used.

The electro-fluidic flow probe can be used in applications where wet wafer-level testing is applicable; however, the electro-fluidic flow probe is not limited to such applications. According to the present invention, the electro-fluidic flow probe is advantageous in nanochannel and nanopore testing as described in detail below. In other embodiments of the present invention, the electro-fluidic flow probe can be used in conventional fluidic probe utilities as known in the relevant art.

According to the present invention, the electro-fluidic flow probe can be used to make electrical measurements for a sequence of nanochannels while the nanochannel is embedded in the wafer.

Figure 2:
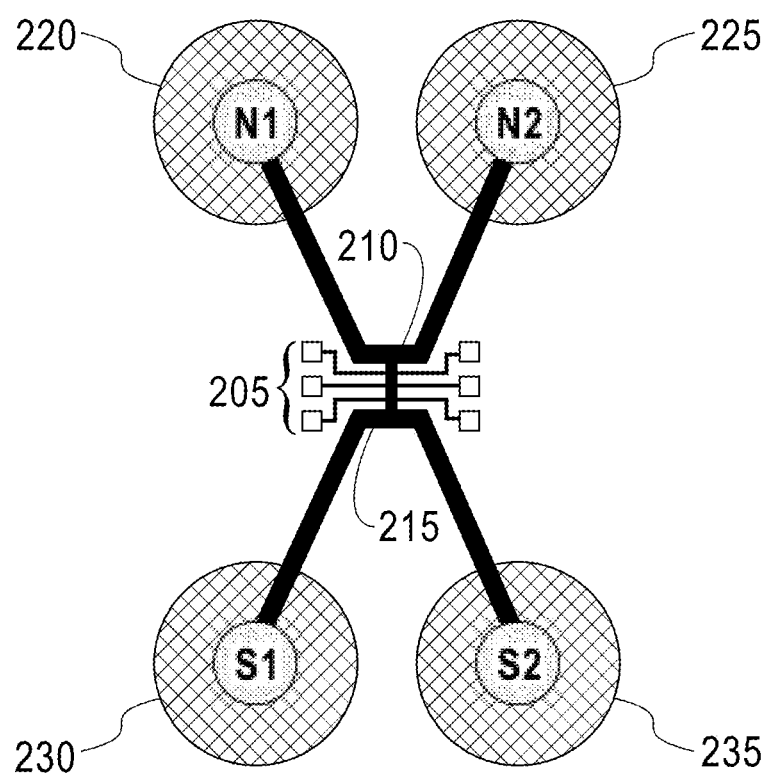
FIG. 2 shows a nanochannel with nanoelectrodes according to a further embodiment of the present invention.

FIG. 2 shows a nanochannel with nanoelectrodes 200 according to an embodiment of the present invention. Nanochannels are generally used in nanofluidic biochips. According to an embodiment of the present invention, the nanochannel is embedded in a wafer. The device under test 205 (DUT) is a nanochannel with nanoelectrodes. The north microchannel 210 has two fluidic ports, first north fluidic port N1 220 and a second north fluidic port, N2 225 as shown in FIG. 2. The south microchannel 215 has two fluidic ports, a first south fluidic port S1 230 and a second south fluidic port S2 235. When testing the ionic current across the nanochannel, a fluidic electrical potential is applied to the microchannels, as described in detail below. The diameter of the fluidic ports and the lengths of the microchannel can vary depending on the specific nanochannel being tested.

In an embodiment of the present invention the inner diameter of the fluidic ports of the nanochannel can range from 0.8 mm to 380 um. The distance between the two north fluidic ports, N1 and N2, can range from 2.0 mm to 6.0 mm. Similarly, the distance between the two south fluidic ports, S1 and S2, can range from 2.0 mm to 6.0 mm. The distance from N2 to S2 and/or N1 and S1 ranges from 2.0 mm to 6 mm. The distance between N1 to S1 and N2 to S2 is preferably, but not limited to, 6.0 mm.

Figure 3:
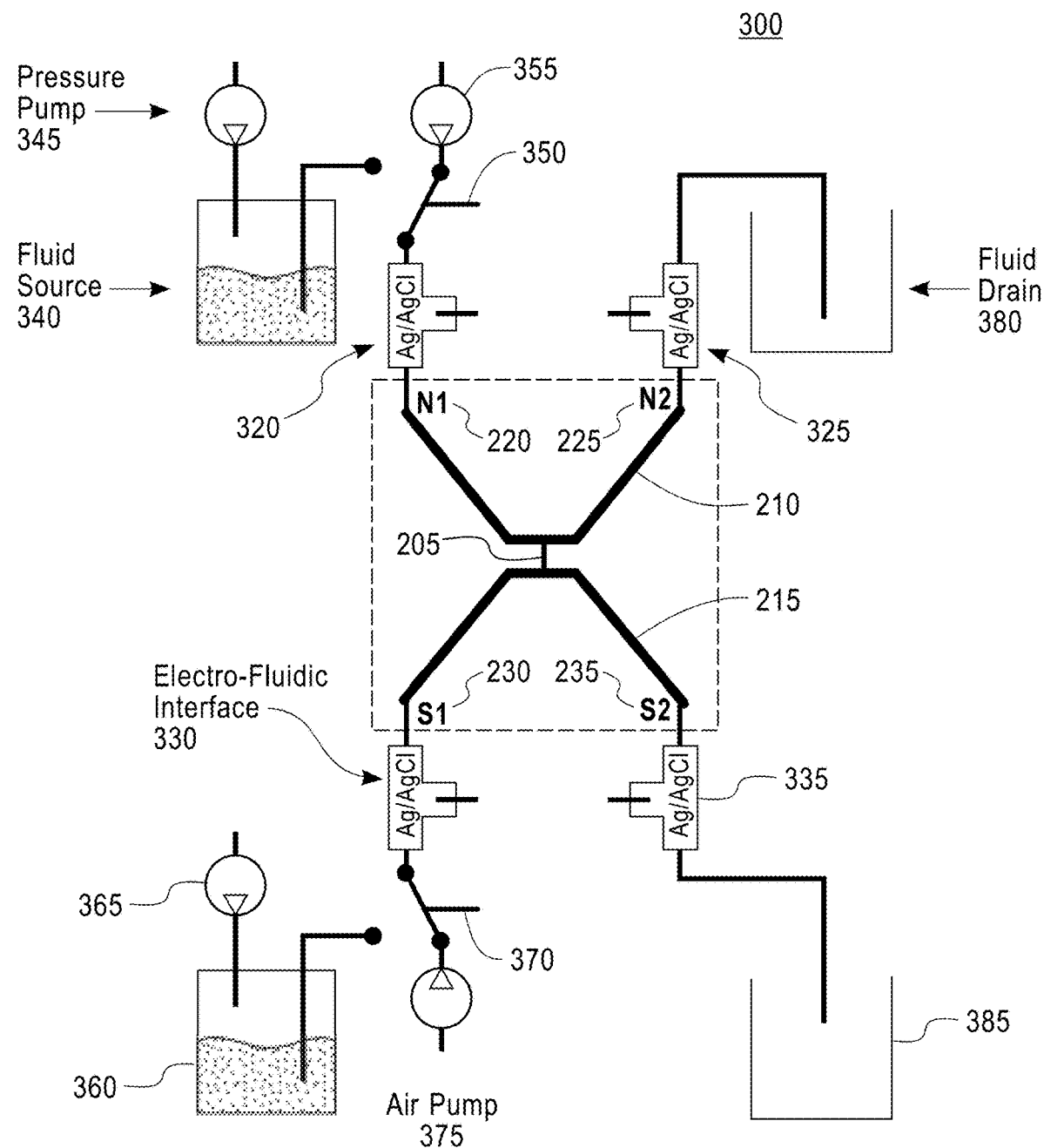
FIG. 3 shows a system for testing a nanochannel according to a further embodiment of the present invention.

FIG. 3 shows a system for wet wafer-level testing of nanochannels according to an embodiment of the present invention. The wafer has at least two devices under test. The device under test (DUT) in test setup 300 is a nanochannel 205. Referring to FIG. 3, there are four electro-fluidic flow probes: a first electro-fluidic flow probe 320, a second electro-fluidic flow probe 330, a third electro-fluidic flow probe 325 and a fourth electro-fluidic flow probe 335. Each of the electro-fluidic flow probes are connected to the four fluidic ports 220, 230, 225 and 235, respectively. The first electro-fluidic flow probe 320 and the second electro-fluidic flow probe 330 that are connected to the first north fluidic port N1 220 and the first south fluidic port S1 230 deliver the electrical potential to the north and south microchannel, respectively. In an embodiment of the present invention, a third electro-fluidic flow probe connected to the second north fluidic port N2 225 and a fourth electro-fluidic flow probe connected to a second south fluidic port S2 235 receive and remove the electrical potential from the microchannels. This is not limited to electro-fluidic flow probes, other fluidic probes can be used to create a leak tight connection with the fluidic ports N2 225 and S2 235 to receive the electrical potential from the microchannels. The electrical connections on each of the electro-fluidic flow probes can be used to verify electrical contacts between the fluidic ports.

FIG. 3 illustrates the test procedure for making electrical measurements of nanochannels according to an embodiment of the present invention. First, fill the north microchannel 210 with electrical potential by using the first electro-fluidic flow probe 320. The first electro-fluidic flow probe 320 receives fluid from the first fluid source 340 by activating the switch 350 so that the first inlet of the first electro-fluidic flow probe 320 can receive a fluid electrolyte from the first fluid source 340. The first fluid source is connected to a first pressure source that facilitates the fluid electrolyte to pass through the first fluid source through the first electro-fluidic flow probe. It is preferred to have distilled water or potassium chloride (KCl) as the fluid electrolyte; however the fluid electrolyte is not limited to such applications.

Referring to FIG. 3, the system includes a switch to make alternating connections from the electro-fluidic flow probe to the either the fluid source or air pressure source to the electro-fluidic flow probe depending on the stage of the process. The present invention is not limited to using switch other methods to establish a connection can be used as known by the ordinary person skilled in the relevant art. Next, verify the filling of the north microchannel with the electrical potential by measuring the current between the electrical connections of the first electro-fluidic flow probe 320 and the third electro-fluidic flow probe 325.

Referring to FIG. 3, fill the south microchannel 215 via electro-fluidic flow probe 330 by connecting the electro-fluidic flow probe to the fluid source 360 by activating the switch 370 so that the first inlet on the electro-fluidic flow probe 330 can receive the fluid from the second fluid source 360. The second fluid source is connected to a second pressure source. The second pressure source facilitates a fluid electrolyte from the second fluid source through the second electro-fluidic flow probe. Next, verify the filling of the south microchannel 215 by measuring the current between the electrical connections on the second electro-fluidic flow probe 330 and the electrical connection on the fourth electro-fluidic flow probe electro-fluidic flow probe 335. Next, verify that the nanochannel has been filled with the electrical potential by measuring the current between the electrical connections on the first electro-fluidic flow probe 320 and the third electro-fluidic flow probe 330 which are connected to fluidic ports N1 220 and S1 230 respectively.

Referring to FIG. 3, after making the electrical measurements, empty the north microchannel 210 with air by connecting the first air pressure source 355 to first electro-fluidic flow probe 320 by activating the switch 350 so that the first inlet of electro-fluidic flow probe 320 is connected to the air pressure source 355. Activate first air pressure source 355 and applying air pressure to remove the electrical potential from the north microchannel. As a result, the electrical potential will flow through fluidic port N2 225 and via electro-fluidic flow probe 325 and it will fill into the drain 380. Similarly, flush the south microchannel 215 with air pressure by connecting a second air pressure source 375 to the second electro-fluidic flow probe 330 by activating switch 370 so that the first inlet of the electro-fluidic flow probe is now connected to the second air pressure source 375. Next, activate second air pressure source 375 and empty the south microchannel by applying air pressure to remove the electrical potential. The electrical potential will flow through second south fluidic port S2 235 and into the fourth electro-fluidic flow probe 335 and fill into the drain 385. After completing the test on the instant nanochannel proceed to the next nanochannel in the wafer.

In another embodiment of the present invention, a probe cart is used to hold the electro-fluidic flow probes in position to deliver the electrical potential to the microchannels. A probe cart can be used to also hold the fluid sources and the air pressure source along with the electro-fluidic flow probe.

In one embodiment of the present invention, the electrical measurement made is the ionic conductivity of the nanochannel which can be used to determine which chips are functional and which are not. This can be done by measuring the pressure difference between the fluidic ports, which determines how much of the liquid with ionic conductivity passes through the nanochannel.

Generally the pressure values and flow rates are dependent on the diameter and lengths of the nanochannels and the diameter and lengths of the microchannels. The filling of the nanochannel is verified when an electrical contact between the north fluidic port and the south fluidic port is established. This generally takes approximately 60 seconds to establish. The filling of the nanochannel needs to be sufficient to produce an electrical contact between the north microchannel and the south microchannel. The pressure sources for the fluid sources generally range from 0 bar to 5 bar during a specific test. To obtain sufficient results the pressure sources are conditioned depending on the dimensions of the specific nanochannel. The pressure values and the volume of the electrical potential delivered in the north and south microchannels are changed according to the specific dimensions of the nanochannels.

According to a further embodiment of the present invention a measuring instrument is used for measuring the current between the first electro-fluidic flow probe and the third electro-fluidic probe to verify the filling of the north microchannel. Similarly the measuring instrument is used for measuring the current between the second electro-fluidic flow probe and the fourth electro-fluidic probe to verify the filling of the south microchannel.

According to another embodiment of the present invention an ionic current map is generated for all of the nanochannels in the wafer. The ionic current map is used to assess which nanochannels are to be considered "bad" chips and non-functional for further use.

Figure 4:
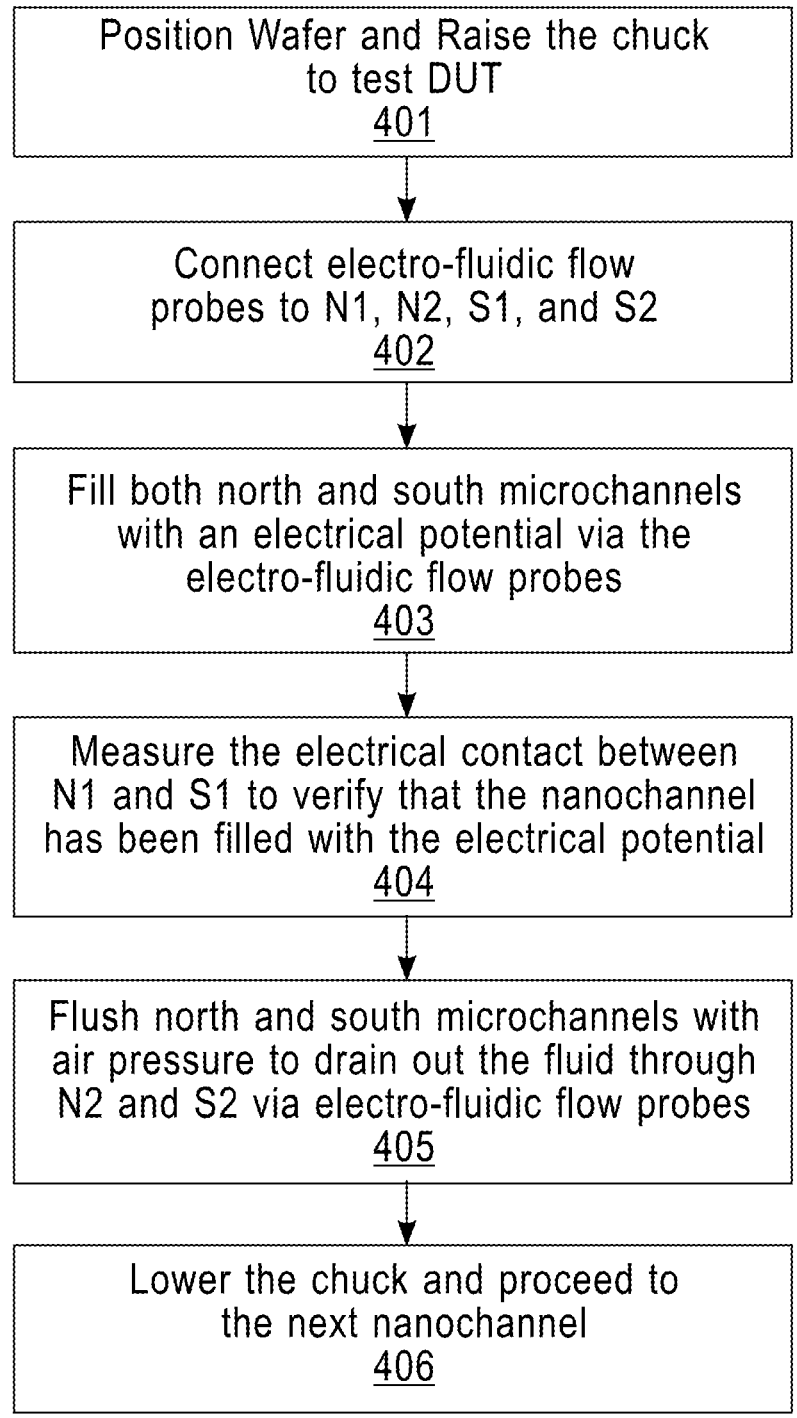
FIG. 4 is a flowchart depicting the procedure for testing a nanochannel according to a further embodiment of the present invention.

FIG. 4 is a flowchart that shows the test procedure for testing a nanochannel according to an embodiment of the present invention. Referring to FIG. 4, step 401 includes positioning the wafer by raising the chuck to test the device under test (DUT), which in this case is the nanochannel. Next, in step 402 connect electro-fluidic flow probes to fluidic ports N1, N2, S1, and S2. Step 403 includes filling both the north microchannel and south microchannel with an electrical potential via the electro-fluidic flow probes. Step 404 includes measuring the electrical contact between N1 and S1 to verify that the nanochannel has been filled with electrical potential. Step 405 includes providing air pressure to the north and south microchannels through fluidic ports N2 and S2 to flush out the electrical potential. The air pressure is provided through the electro-fluidic flow probes that are connected to N1 and S1. Step 406 includes lowering the chuck and proceeding to the next nanochannel.

According to a further embodiment of the present invention, the electro-fluidic flow probe can be used to make electrical measurements for a sequence of nanopores in a wafer.

Figure 5:
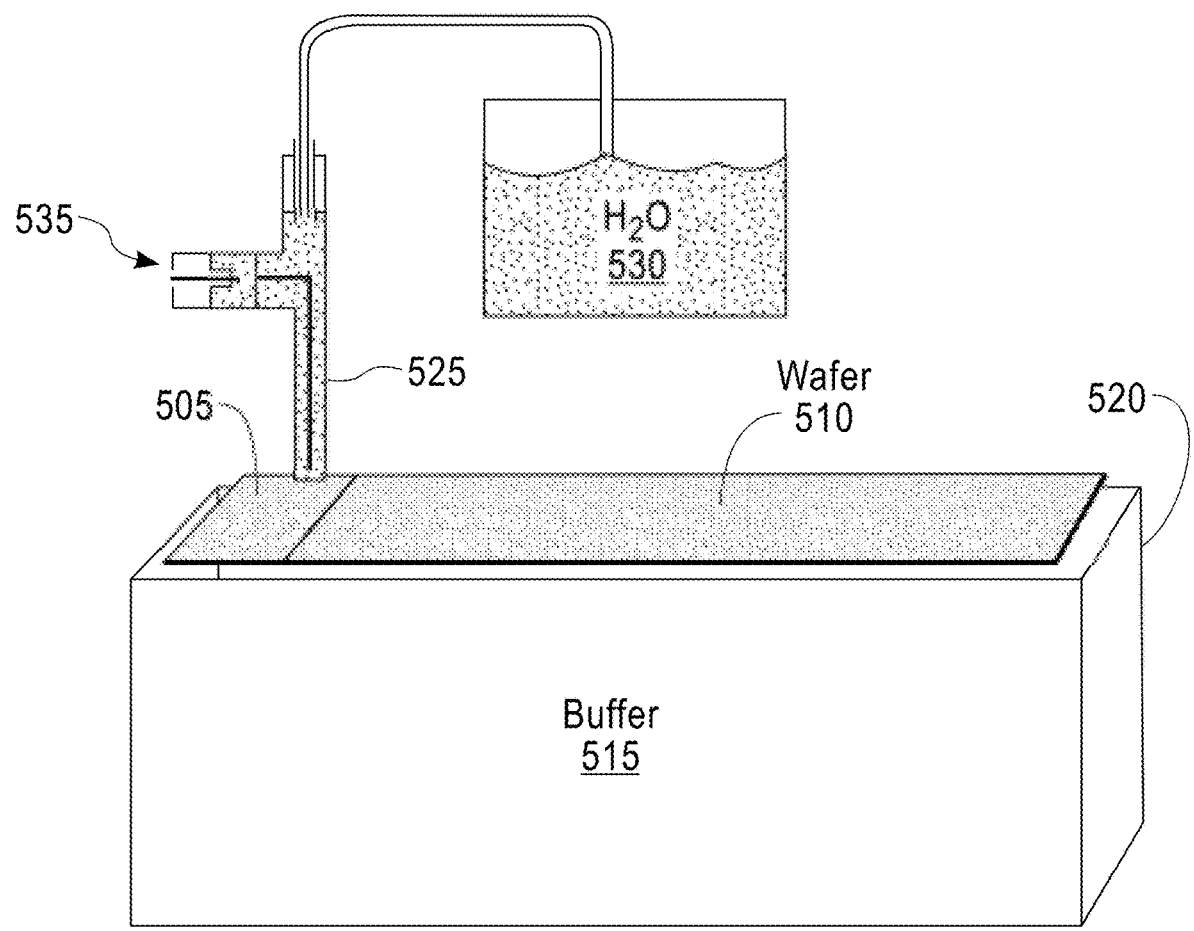
FIG. 5 shows a system for testing a nanopore according to a further embodiment of the present invention.

FIG. 5 shows a system for testing nanopores embedded in a wafer. More specifically, for measuring the ionic conductivity of the nanopores to determine which chips are functional for future use. However, the method is not limited to such applications and can be used in other electrical measurements as known to the ordinary person skilled in the relevant art. Referring to FIG. 5, the testing bath 520 is filled with distilled water. It is preferred for the testing bath to be filled with distilled water; however other diluted solutions can be used to fill the testing bath. The solution in the testing bath is the liquid buffer that comes into contact with the electrical potential. Next, the wafer 510 is soaked with isopropyl alcohol. The isopropyl alcohol allows the nanopore embedded in the wafer 505 to absorb the electrical potential to create an electrical contact with the liquid buffer 515. The wafer is placed in the isopropyl alcohol for a few seconds or a sufficient amount of time to wet the inside of the nanopore. The wafer 510 is then placed on top of the liquid buffer. The wafer 510 includes at least two nanopores.

Referring to FIG. 5, the first nanopore 505 is being tested. The electro-fluidic flow probe 525 is positioned precisely on top of the nanopore 505 so that the nanopore can absorb the electrical potential. The electro-fluidic flow probe 525 is attached to a fluid source 530 for the input of the liquid. The fluid source includes a fluid electrolyte which can be any liquid with ionic conductivity. It is preferred to have distilled water; however other solutions can be used to apply the electrical potential to the nanopore as known to the person with ordinary skill in the relevant art. The fluid source is connected to a pressure source to facilitate the fluid electrolyte to pass from the fluid source and through the electro-fluidic flow probe.

As discussed above, the electro-fluidic bias tee inside the electro-fluidic flow probe merges the electrical connection 535 and the fluid electrolyte inside the electro-fluidic flow probe to create a fluidic electrical potential. Once the electrical potential is applied to the nanopore it creates an electrical contact with the liquid buffer. As a result the ionic conductivity of the nanopore is measured.

The amount of electrical potential depends on the diameter and lengths of the nanopore being tested. Furthermore, the amount of electrical potential that is applied to the nanopore should be sufficient to create an electrical contact with the liquid buffer.

In another embodiment of the present invention, a pick and place method is utilized to further establish accurate measurements in nanopore wafer-level testing. The pick and place method includes a conventional probe or an electro-fluidic flow probe that follows the electro-fluidic flow probe and picks up the liquid that remains between the different nanopores on the wafer when applying the electrical potential from the electro-fluidic flow probe. The pick and place method ensures that there are minimal shortages between the nanopores to optimize the accuracy of the electrical measurements of the nanopores.

FIG. 6 shows an electronically generated ionic current map of the wafer once the testing is completed. The map can be generated in approximately 10 seconds after the completion of the test on the last nanopore in the wafer and assists in assessing which chips are functional usable chips. The map can illustrate with colors the ionic conductivity of different nanopores. Referring to FIG. 6, each box on the map includes the identification number of the nanopore and the current measured. For example, the nanopore 605 includes the nanopore number, which is 21, and has an ionic current of 10 nA. This allows the reader of the map to determine which chips are functional and usable and which chips are non-usable and are considered "bad" chips. The generation of the current maps are not limited to current measurements, but can be used in applications as known in the relevant art.

Figure 7:
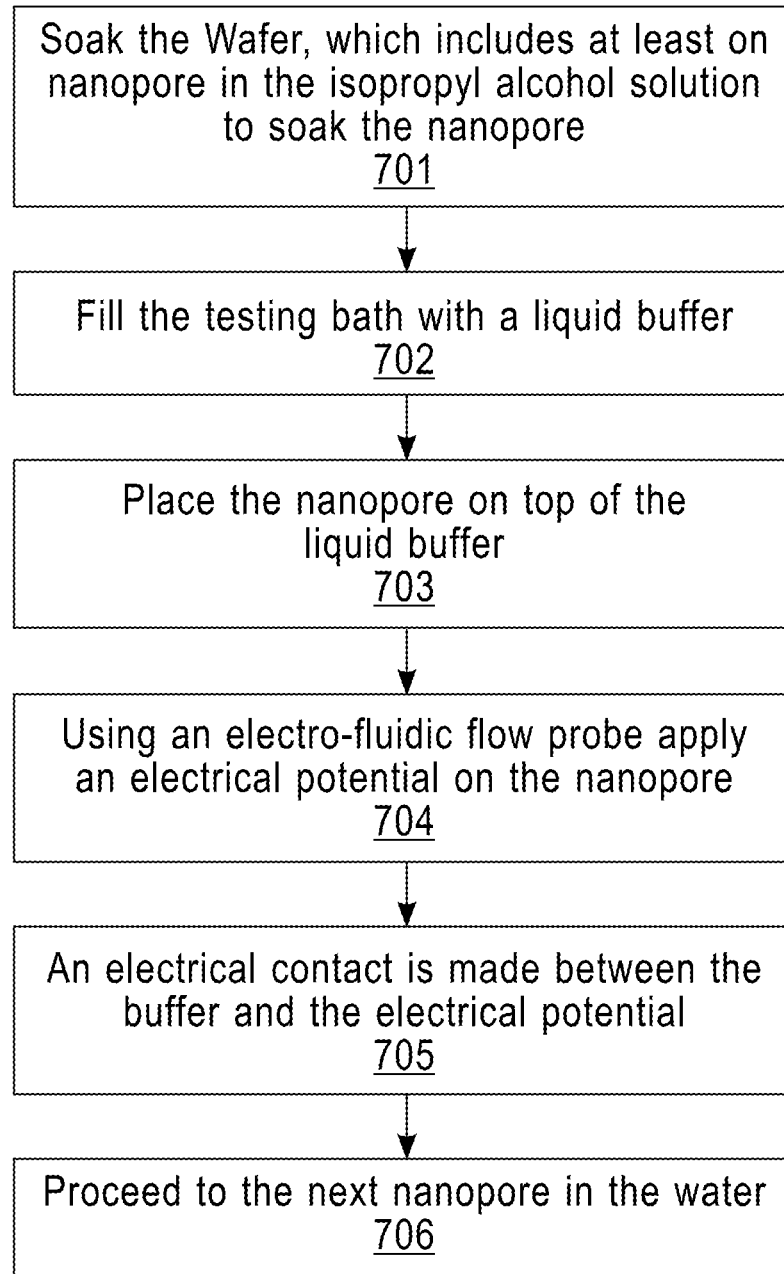
FIG. 7 is a flowchart depicting the procedure for testing a nanopore according to a further embodiment of the present invention.

FIG. 7 depicts a flowchart for a test procedure for testing a nanopore embedded in a wafer according to an embodiment of the present invention. In step 701, the nanopore is soaked in isopropyl alcohol solution. The isopropyl alcohol solution wets the inside of the nanopore and allows an electrical potential to be absorbed by the nanopore to allow an electrical contact with the liquid buffer. Solutions other than isopropyl alcohol can be used in step 701, as known in the relevant art. Step 702 includes filling the testing bath with a liquid buffer. It is preferred to use distilled water, however other diluted solution can be used as known in the relevant art. Step 703 includes placing the wafer with the embedded nanopores on top of the buffer. Step 704 includes using an electro-fluidic flow probe to apply a droplet of the electrical potential on the nanopore. Step 705 includes making an electrical contact between the buffer and the electrical potential. Step 706 includes proceeding to test the next nanopore in the wafer.

According to another embodiment of the present invention a mechanical arm is used to apply the electrical potential on the nanopore. A mechanical arm holds and positions the electro-fluidic flow probe so that it can apply the electrical potential with precision to each nanopore. Once the electrical potential is applied, and the resulting current is read, the measurement can be replicated on the next nanopore.

According to a further embodiment of the present invention the nanopore testing is done in the field of biomaterials. Nanopores are used in many chemical and bio-molecular sensing. In these applications, the collective behavior of all the pores in the nanoporous material or thin film is of primary interest.

According to the present invention, nanopores can be approximately 50 nm long and have a diameter that ranges from 5 nm to 40 nm. The space between each nanopore can vary according to the design, but is generally between 5 mm to 10 mm. According to an embodiment of the present invention, the electro-fluidic flow probe has an outlet of a diameter of 1.5 mm when testing a nanopore. However, the outlet of the electro-fluidic flow probe for nanopore testing will range according to the design of the nanopore.

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements that can be found in the claims below are intended to include any structure, material, or act for performing the function in combination with other claimed elements as specifically claimed. The description of the present invention has been presented for purposes of illustration and description, but is not intended to be exhaustive or limited to the present invention in the form disclosed. Many modifications and variations will be apparent to those of ordinary skill in the art without departing from the scope and spirit of the present invention. The embodiments were chosen and described in order to best explain the principles of the present invention and the practical application, and to enable others of ordinary skill in the art to understand the present invention for various embodiments with various modifications as are suited to the particular use contemplated.

What is claimed is:

1. A method for testing a nanochannel in a wafer, the method comprising:
    connecting a first electro-fluidic flow probe to a first north fluidic port of a north microchannel, the first electro-fluidic flow probe comprising a body portion for receiving a fluid electrolyte from a first fluid source, a first inlet including a tube for receiving the fluid electrolyte extending from the first inlet to an outlet through an electro-fluidic bias tee, and a second inlet, the first inlet of the electro-fluidic bias tee being connected to a switch and in communication with the first fluid source through the switch, the first inlet configured to alternate between receiving the fluid electrolyte from the first fluid source through the switch and receiving air pressure from an air pressure source through the switch, the tube being both in direct contact with the electro-fluidic bias tee and distinct from the electro-fluidic bias tee;
    connecting a second electro-fluidic flow probe to a first south fluidic port of a south microchannel, wherein the north microchannel is coupled to the south microchannel through the nanochannel;
    filling the north microchannel with an electrical potential, wherein the electrical potential is delivered from the first electro-fluidic flow probe to the first north fluidic port and into the north microchannel;
    filling the south microchannel with an electrical potential, wherein the electrical potential is delivered from the second electro-fluidic flow probe to the first south fluidic port and into the south microchannel;
    measuring a current via the fluid electrolyte between the first electro-fluidic flow probe and the second electro-fluidic flow probe via the nanochannel to determine that the nanochannel is functional.

2. The method according to claim 1, wherein the first fluid source is connected to a first pressure source, wherein the first pressure source passes the fluid electrolyte from the first fluid source through the first electro-fluidic flow probe.

3. The method according to claim 1, wherein the second electro-fluidic flow probe is connected to a second fluid source that is connected to a second pressure source, and wherein the second pressure source passes a fluid electrolyte from the second fluid source through the second electro-fluidic flow probe.

4. The method according to claim 1, further comprising:
    connecting a third electro-fluidic flow probe to a second north fluidic port of the north microchannel; and
    connecting a fourth electro-fluidic flow probe to a second south fluidic port of the south microchannel.

5. The method according to claim 4, further comprising:
    emptying the electrical potential from the north microchannel via the third electro-fluidic flow probe, wherein the electrical potential passes through the second north fluidic port and through the third electro-fluidic flow probe; and
    emptying the electrical potential from the south microchannel via the fourth electro-fluidic flow probe, wherein the electrical potential passes through the second south fluidic port and through the fourth electro-fluidic flow probe.

6. The method according to claim 4, wherein:
    the third electro-fluidic flow probe is connected to a first drain for draining the electrical potential; and
    the fourth electro-fluidic flow probe is connected to a second drain for draining the electrical potential.

7. The method according to claim 5, further comprising:
    connecting the first electro-fluidic flow probe to a first air pressure source, wherein the first air pressure source applies air pressure into the north microchannel and passes the electrical potential through the second north fluidic port and into the third electro-fluidic flow probe.

8. The method according to claim 5, further comprising:
    connecting the second electro-fluidic flow probe to a second air pressure source, wherein the second air pressure source applies air pressure into the south microchannel and passes the electrical potential through the second south fluidic port and into the fourth electro-fluidic flow probe.

9. The method according to claim 1, wherein the wafer comprises a plurality of nanochannels, the method further comprising:
generating an ionic current map for each nanochannel in the wafer.

10. The method according to claim 1, further comprising:
measuring the current between the first electro-fluidic flow probe and the third electro-fluidic probe to verify the filling of the north microchannel; and
measuring the current between the second electro-fluidic flow probe and the fourth electro-fluidic probe to verify the filling of the south microchannel.

11. The method according to claim 1, wherein the wafer comprises a plurality of nanochannels, the method further comprising:
positioning the nanochannel relative to the north microchannel and the south microchannel; and
testing another nanochannel in the wafer after completing measurement of the current between the first electro-fluidic flow probe and the second electro-fluidic flow probe, the testing another nanochannel in the wafer including positioning the another nanochannel relative to the north microchannel and the south microchannel.

12. The method according to claim 1, wherein the electro-fluidic bias tee is remote from the fluid source and is not in the fluid source.

13. The method according to claim 1, wherein inner surfaces of the tube contain the wire while outer surfaces of the tube are not in contact with the wire; and
wherein the first inlet is coupled to the fluid source through the switch.

* * * * *